United States Patent
Augustine et al.

(10) Patent No.: US 7,101,389 B1
(45) Date of Patent: *Sep. 5, 2006

(54) INFLATABLE LOWER BODY THERMAL BLANKET

(75) Inventors: Scott D. Augustine, Bloomington, MN (US); Randall C. Arnold, Maplewood, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/419,719

(22) Filed: Apr. 10, 1995

Related U.S. Application Data

(63) Continuation of application No. 07/638,748, filed on Jan. 8, 1991, now Pat. No. 5,405,371, which is a continuation-in-part of application No. 07/550,757, filed on Jul. 10, 1990, now abandoned, which is a continuation-in-part of application No. 07/227,189, filed on Aug. 2, 1988, now abandoned, which is a continuation-in-part of application No. 07/104,682, filed on Oct. 5, 1987, now abandoned.

(51) Int. Cl.
*A61F 7/00* (2006.01)

(52) U.S. Cl. ..................................... 607/107

(58) Field of Classification Search ................ 607/104, 607/107, 108, 112; 165/46; 5/482, 485
See application file for complete search history.

(56) References Cited

U.S. PATENT DOCUMENTS

| | | | | |
|---|---|---|---|---|
| 222,690 | A | 12/1879 | Goldschmidt | 128/403 |
| 1,399,095 | A | 12/1921 | Webb, Sr. | 128/402 |
| 1,777,982 | A | 10/1930 | Popp | 128/399 |
| 2,093,834 | A | 9/1937 | Gaugler | 128/402 |
| 2,110,022 | A * | 3/1938 | Kliesrath | 607/107 |
| 2,512,559 | A | 6/1950 | Williams | 5/347 |
| 2,601,189 | A | 6/1952 | Wales, Jr. | 4/160 |
| 2,706,988 | A | 4/1955 | Weber | 128/402 |
| 3,418,726 | A | 12/1968 | Sparks | 34/99 |
| 3,610,251 | A | 10/1971 | Sanderson | 128/379 |
| 3,714,947 | A | 2/1973 | Hardy | 128/400 |
| 4,572,188 | A * | 2/1986 | Augustine | 607/107 |
| 4,660,388 | A * | 4/1987 | Greene | 5/485 |

(Continued)

FOREIGN PATENT DOCUMENTS

DE   3308553   3/1983

(Continued)

OTHER PUBLICATIONS

Ninth New Collegiate Dictionary, regarding laminate.

(Continued)

*Primary Examiner*—Mark S. Graham
(74) *Attorney, Agent, or Firm*—Incaplaw; Terrance A. Meador

(57) ABSTRACT

A thermal blanket includes an inflatable covering with a head end, a foot end, two edges, and an undersurface. The covering includes a plurality of inflatable chambers that are inflated when a thermal-controlled inflating medium is introduced into the thermal blanket through an inlet at the foot end. When inflated, the thermal blanket self-erects into a structure and provides a bath of thermally-controlled inflating medium to the interior of the erected structure through an aperture array on the undersurface of the inflatable covering. The thermal blanket is constructed for substantially longitudinal disposition over a portion of a patient's body extending from the pelvic area to the feet of the patient's body. Provision may be made for securing the inflatable covering to the patient's body at the head end. Provision may further be made for an uninflatable foot drape at the foot end.

10 Claims, 5 Drawing Sheets

U.S. PATENT DOCUMENTS 4,807,644 A * 2/1989 Sandhaus ................... 128/853
5,324,320 A * 6/1994 Augustine et al. .......... 607/107

FOREIGN PATENT DOCUMENTS

EP 88309191.0 10/1988

OTHER PUBLICATIONS

Webster's Third New International Dictionary, p. 250, regarding bond.
McGraw-Hill Encyclopedia of Science & Technology, 7th Edition, p. 713, regarding bonding.
Search Report in EPO Patent Application EPO 88309191.0.
Deposition of Randall C. Arnold in *Mallinckrodt Medical, Inc. v. Augustine Medical, Inc.*, Case No. 4:95CV00514 LOD, Eastern District of Missouri, Eastern Division, Feb. 27, 1996.
Photograph Exhibit No. 1 of Deposition of Randall C. Arnold.
Photograph Exhibit No. 2 of Deposition of Randall C. Arnold.
Photograph Exhibit No. 3 of Deposition of Randall C. Arnold.
"Normothermia In The O.R.", Exhibit No. 4 of Deposition of Randall C. Arnold.
Memorandum In Support Of Defendant's Motion For Partial Summary Judgement Of Non-Infringement in *Augustine Medical, Inc., Plaintiff v. Mallinckrodt Group, Inc. and Mallinckrodt Medical, Inc., Defendants*, Case No. 4-94-875, United States District Court, District of Minnesota, Fourth Division. pp. 19-25.
Report and Recommendation of magistrate Judge Franklin L. Noel in *Augustine Medical, Inc., Plaintiff v. Mallinckrodt Group, Inc. and Mallinckrodt Medical, Inc., Defendants*, Case No. 4-94-875, United States District Court, District of Minnesota, Fourth Division. pp. 1-19.
Memorandum In Support of Defendants' Motion For Partial Summary Judgment, *Augustine Medical, Inc., Plaintiff v. Mallinckrodt Group, Inc. and Mallinckrodt Medical, Inc., Defendants*, Case No. 4-94-CV-875, U.S. District Court, District of Minnesota, Fourth Division.
Memorandum of Augustine Medical, Inc., *Augustine Medical, Inc., Plaintiff v. Mallinckrodt Group, Inc. and Mallinckrodt Medical, Inc., Defendants*, Case No. 4-94-CV-875, U.S. District Court, District of Minnesota, Fourth Division.
Defendants' Reply To Memorandum Of Augustine Medical, Inc., *Augustine Medical, Inc., Plaintiff v. Mallinckrodt Group, Inc. and Mallinckrodt Medical, Inc., Defendants*, Case No. 4-94-CV-875, U.S. District Court, District of Minnesota, Fourth Division.
US Court of Appeals For The Federal Circuit, DECISION, dated Jun. 8, 1999, *Augustine Medical, Inc., vs. Gaymar Industries, Inc. and Medisearch PR, Inc., and Mallinckrodt Group, Inc. and Mallinckrodt Medical, Inc.*, 98-1001, -1002, -1054, -1244, -1266, Jun. 8, 1999.
US Court of Appeals For The Federal Circuit, Combined Petition for Rehearing and Suggestion for Rehearing in Banc of Plaintiff-Cross-Appellant Augustine Medical, Inc., *Augustine Medical, Inc. v. Gaymar Industries, Inc. and Medisearch P R, Inc. and Mallinckrodt Group, Inc. and Mallinckrodt Medical, Inc.*, 94-CV-875, 94-CV-888, 96-CV-347 and 96-CV-1145, Jun. 21, 1999.
Communication dated Oct. 21, 1997 by Craig J. Lervick, Oppenheimer, Wolff & Donnelly.
Decision, Sua Sponte, To Merge Reexamination and Reissue Proceedings for In re reissue application of Augustine, et al, U.S. Appl. No. 08/658,356, filed Jun. 5, 1996, For U.S. Patent No. 5,405,371 and In re Augustine et al, Reexamination Proceeding, Control No. 90/004,529, Filed Jan. 23, 1997, For U.S. Patent No. 5,405,371.

\* cited by examiner

INFLATABLE LOWER BODY THERMAL BLANKET

RELATED APPLICATIONS

This application is a continuation of application Ser. No. 07/638,748, filed Jan. 8, 1991, U.S. Pat. No. 5,405,371 is a continuation-in-part of application Ser. No. 07,550,757, filed Jul. 10, 1990, abandoned, which is a continuation-in-part of application Ser. No. 07/227,189, filed Aug. 2, 1988, abandoned, which is a continuation-in-part of application Ser. No. 07,104,682, filed Oct. 5, 1987, abandoned.

This application is related to copending U.S. patent application Ser. Nos. 08/386,324; 08/388,730; and 08/419,718.

BACKGROUND OF THE INVENTION

This invention relates to thermal blankets used in a medical setting to deliver a bath of a thermally-controlled medium to a patient.

The thermal blanket prior art is best expressed in our prior U.S. Pat. No. 4,572,188 entitled "AIRFLOW COVER FOR CONTROLLING BODY TEMPERATURE." In our prior patent, a self-erecting, inflatable airflow cover is inflated by the introduction into the cover of a thermally-controlled inflating medium, such as warmed air. When inflated, the cover self-erects about a patient, thereby creating an ambient environment about the patient, the thermal characteristics of which are determined by the temperature of the inflating medium. Holes on the underside of our prior art airflow cover exhaust the thermally-controlled, inflating medium from inside the cover to the interior of the erected structure. Our airflow cover is intended for the treatment of hypothermia, as might occur postoperatively.

Evaluation of our airflow cover by skilled practitioners has resulted in general approbation: the opinion is that the airflow cover efficiently and effectively accomplishes its purpose of giving a thermally-controlled bath. We have realized, however, that, while our prior art airflow cover achieves its objective, certain improvements to it are necessary in order to realize additional clinical objectives and to enjoy further advantages in its use.

SUMMARY OF THE INVENTION

We have improved the clinical usefulness of our self-erecting airflow cover by observing that controlling the contour of its inflatable portion at its head end to define a generally concave non-inflatable portion will permit a care giver to more easily observe a patent's head, face, neck and chest. Further, we have observed that limited venting of the thermally controlled inflating medium from the edges of the cover results in more efficient, more uniform heating within the cover. We have also observed that it is good clinical practice to keep the area of the care site in the vicinity of the patient's head and face as clean as possible. Still further, we have observed that modification of the foot end of the self-erecting airflow cover to define a non-inflatable but erectable drape section retains heat from the inflating medium to warm the patient's feet and insulate the bare skin of the feet from excessive heat from the inlet hose. Finally, we have observed that our self-erecting airflow cover may be advantageously adapted to thermally control specific partial portions of the patient such as the legs and lower body or the arms and upper body, leaving other areas of the patient available for care and treatment. Moreover, an end portion of the cover may be adhesively attached to the patient to prevent the migration of air toward a care area. Finally, a protective sleeve may be slideably mounted on a connected heater tube adjacent the patient to prevent the heater tube from contacting the patient.

These observations have resulted in an improved thermal blanket and method therefor in which a self-erecting inflatable covering has a head end, a foot end, two edges, and an undersurface. An inflating inlet adjacent the foot (or head) end admits a thermally-controlled inflating medium into the covering. An aperture array on the undersurface of the covering exhausts the thermally controlled inflating medium from the covering into the structure created when the covering self-erects upon inflation. The improvements to this basic structural complement include an uninflatable section at the head (or foot) end of the covering, exhaust port openings at the edges of the covering, an absorbent bib or adhesive strip attached to the covering at the head (or foot) end adjacent the uninflatable section, an uninflatable erectable drape section at the foot end of the covering, a heater tube protective cover and structural features that make the covering simple and economical to produce. In the case of an upper body covering, the positions of the inflating inlet and the uninflatable section are reversed from that of other coverings. In the case of an upper body covering, the inflating inlet is positioned at the head end of the covering while the uninflatable section is arranged at the foot end of the covering.

With these improvements, the thermal blanket, when inflated and erected over a patient, delivers the thermally-controlled inflating medium into the interior of the structure covering the patient, thereby thermally bathing the patient. The first improvement permits full viewing of the head and face of the patient from almost any aspect around the thermal blanket. The exhaust port openings increase the rate of circulation of the inflating medium within the blanket, thereby increasing the temperature within the structure and making the temperature distribution more uniform. The absorbent bib soaks up and retains liquids which might otherwise spread over the care site in the area of a patient's head or other body area. Such liquids can include the patient's own perspiration, blood, vomit, saliva, or liquids which are administered to the patient. The adhesive strip acts to seal the head (or foot) end of the inflated structure. The non-inflatable erectable drape section at the foot end of a covering encompassing the lower extremities retains heat around the patient's feet and insulates the bare skin of the legs and/or feet. The protective cover for the heater tube prevents an attached heater tube from contacting the patient.

From another aspect, the invention is a thermal blanket for covering and bathing a person in a thermally-controlled medium. The thermal blanket includes a flexible base sheet having a head end, a foot end, two edges, and a plurality of apertures opening between the first and second surface of the base sheet. An overlying material sheet is attached to the first surface of the base sheet by a plurality of discontinuous seams which form the material sheet into a plurality of substantially parallel, inflatable chambers. A continuous seam is provided between the material sheet and the base sheet at the head (or foot) end to form a non-inflatable viewing recess at the head (or foot) end. Exhaust port openings are provided through the material sheet to vent the medium from the chambers away from the base sheet. An absorbent bib is attached to the head (or foot) end in the vicinity of the viewing recess. In coverings encompassing the lower extremities, a continuous seam is provided between the material sheet and the base sheet at the foot end to form a non-inflatable, erectable drape section to cover the patient's legs and/or feet.

Therefore the invention accomplishes the important objective of providing a self-erecting, inflatable thermal blanket that permits a relatively unobstructed view of a care site when in use.

Another objective is the efficient and uniform heating of the interior of the structure created when the blanket is inflated with a heat inflating medium.

A further objective is providing a covering for a patient's legs and/or feet that helps retain the heat inflating medium around the patient.

A still further objective is the provision of such a blanket with a means for maintaining the cleanliness of the care site.

A still further objective is to provide the ability to select coverings adapted for specific partial areas of the patient leaving other areas exposed for care and treatment.

The advantageous simplified structure of the thermal blanket make its production straight forward and economical.

These and other important objectives and advantages will become evident when the detailed description of the invention is read with reference to the below-summarized drawings, in which.

DETAILED DESCRIPTION OF THE PREFERRED EMBODIMENTS

When used herein, the term "thermal blanket" is intended to be interchangeable with, but not necessarily limited by, the term "airflow cover" used in our U.S. Pat. No. 4,572,188, which is incorporated herein in its entirety by reference. In this description, the term "thermal blanket" is meant to invoke a self-erecting, inflatable structure for delivering a thermally-controlled inflating medium to the interior of the structure created when the thermal blanket is inflated. The purpose of the thermal blanket is to efficiently administer a uniformly thermally-controlled bath of the inflating medium to a patient within the erected structure.

Figure 1:
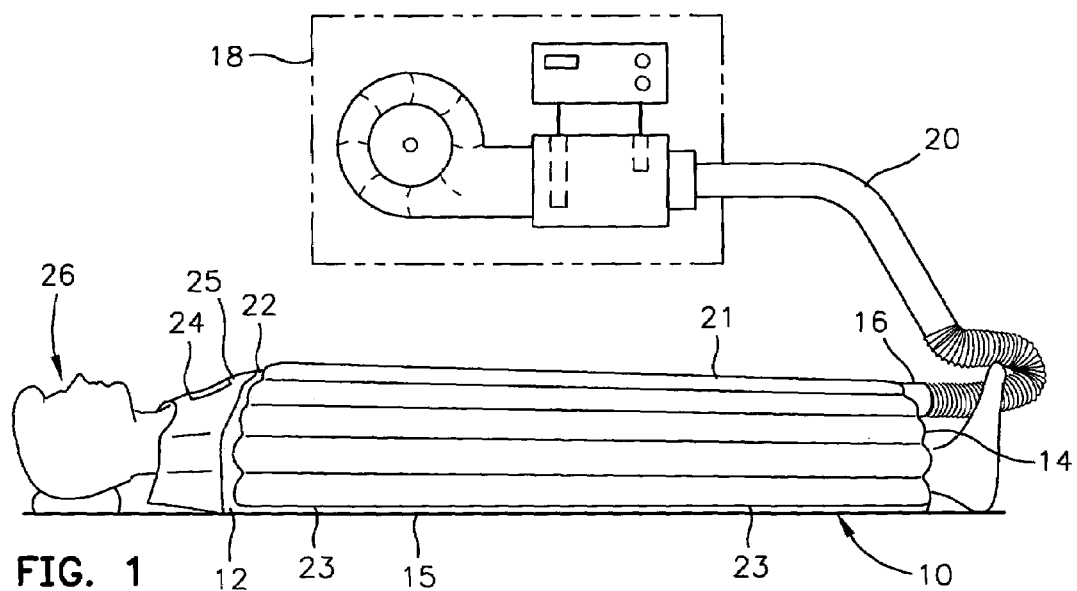
FIG. 1 is a side elevation view of a thermal blanket constructed in accordance with a first aspect of the invention, with the blanket in use, with associated thermal apparatus indicated schematically.

Our invention is illustrated as we intend for it to be used in a first aspect without a foot drape in FIG. 1. In FIG. 1, a self-erecting, inflatable thermal blanket 10 has a head end 12, a foot end 14 and two lateral edges, one indicated by 15. An inflation inlet cuff 16 is connected to a heater/blower assembly 18 which provides a stream of heated air through a connecting hose 20. When the heater/blower 18 is operated, the stream of heated air flows through the inflating hose 20 into the thermal blanket 10 through the inflation cuff 16. When the blanket is inflated, it erects itself into a Quonset hut-like structure with a quilted upper surface 21. As described below, a pattern of apertures on the undersurface of the blanket (not shown in FIG. 1) convectively delivers the inflating heated air into the interior space enclosed by the erected thermal blanket.

The contour of the inflatable portion of the thermal blanket 10 is varied at the head end 12 of the blanket to provide a non-inflated blanket recess 22 in the quilted upper surface 21, which remains smooth and flat when the blanket is inflated and erected. Circulation of the heating air is accelerated through the thermal blanket by exhaust port openings in the upper surface, adjacent the lateral edges of the blanket. Two exhaust ports openings are indicated by reference numeral 23. Further, a bib 24 made of an absorbent material is attached to the head end 12 of the thermal blanket in the vicinity of the non-inflated recess 22. In fact, as shown in FIG. 1, the bib 24 includes a semi-circular tab 25 that extends into the recess 22.

As illustrated in FIG. 1, the thermal blanket of the invention is inflated, erects itself into a bathing structure, and bathes a patient 26 with the thermally-controlled air used to inflate the structure. While the patient is being thermally bathed, the uninflated recess 22 permits observation of the patient's head, face, neck, and chest from almost any location with respect to the thermal blanket 10. Thus, if the patient is placed on a gurney or a bed, the head of which is against a wall, a care giver such as a nurse, intern, resident, or doctor, can keep the patient's face under observation from the foot end 14 of the thermal blanket 10. Respiration can be detected by the rise and fall of the bib and uninflated area, which rest directly on the patient's chest. Moreover, the bib 24 will provide an absorbent sink for stray, unconfined liquids in the area of the patient's head or at the head end 12 of the thermal blanket 10.

Figure 2:
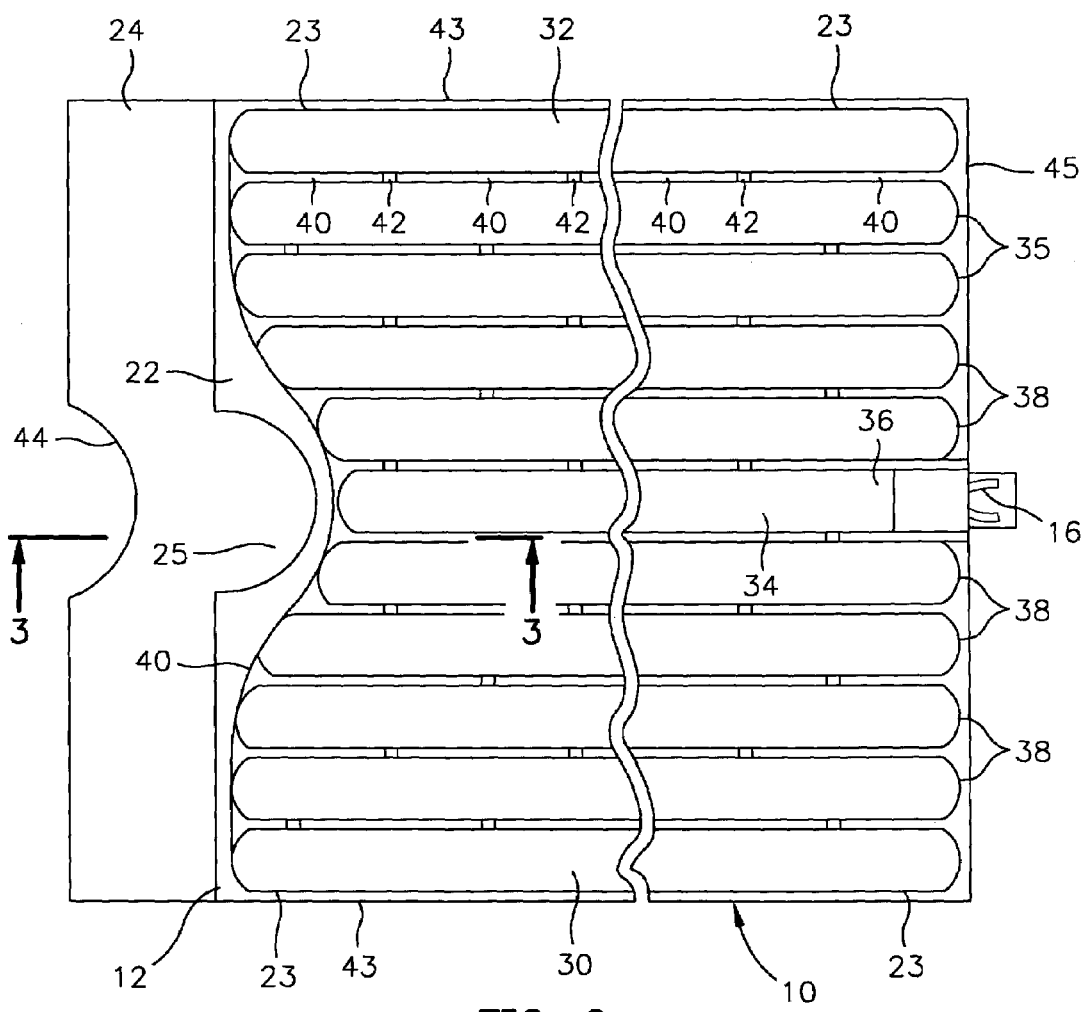
FIG. 2 is an enlarged top plan view of the thermal blanket opened flat.

FIG. 2 is a plan view of the thermal blanket 10 opened flat to show details of its structure. FIG. 2 illustrates the upper surface of the thermal blanket, that is the side that is visible in FIG. 1. As seen, the upper surface consists of a parallel array of elongated tubes of which 30 and 32 are the lateralmost tubes, 34 is the center tube, and the tubes 38 are arrayed between one of the lateralmost tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the thermal blanket, when inflated, to assume a tubular structure on the upper surface, while the ports 42 permit full circulation of the inflating medium throughout the array of tubes. The foot-end seam 45 is continuous. The tubes are inflated through the center tube 34 which transitions to a port 36, through which the inflation cuff 16 is inserted. The edge seams 43 are discontinuous only at the exhaust port opening locations 23.

A seal can be made between the inflation port 36 and the inflation cuff 16 by any conventional means, for example, an o-ring, or even tape. When the inflating medium is introduced into the center tube 34, it flows laterally from the center tube into all of the other tubes through the ports 42. Near the head end 12, a continuous seam 40 defines the forward end of all of the tubes, with the seam assuming a bell-curve shape. On the head end side of the seam 40, the thermal blanket 10 is uninflatable. The bell-shaped seam 40 thus defines the uninflatable area 22 at the head end of the thermal blanket 10, which is essentially coplanar with, or substantially parallel to, the underside of the blanket. As shown in FIG. 1, by virtue of its structural integration with the rest of the thermal blanket 10, the non-inflated recess extends over the upper chest of the patient 26 when the blanket is inflated. However, since the recess 22 is uninflated, it provides a wide-angled viewing gap in the inflated contour of the upper surface 21. The gap is filled by continuation of the underside of the blanket. It is also noted that the pattern of inflatable tubes can be replaced by other suitable patterns of communicating, inflatable chambers. The tubes are preferred since they impart strength and shape to the erected bathing structure; other inflatable structures are contemplated, however.

The absorbent bib has an indent 44 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
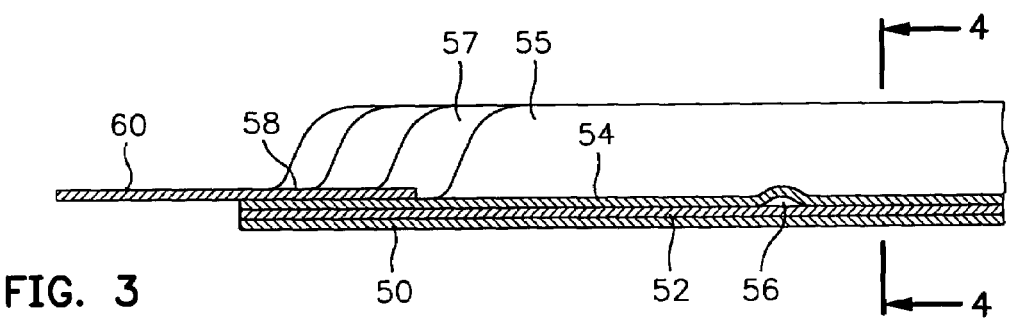
FIG. 3 is an enlarged sectional view taken along 3—3 of FIG. 2.
Figure 4:
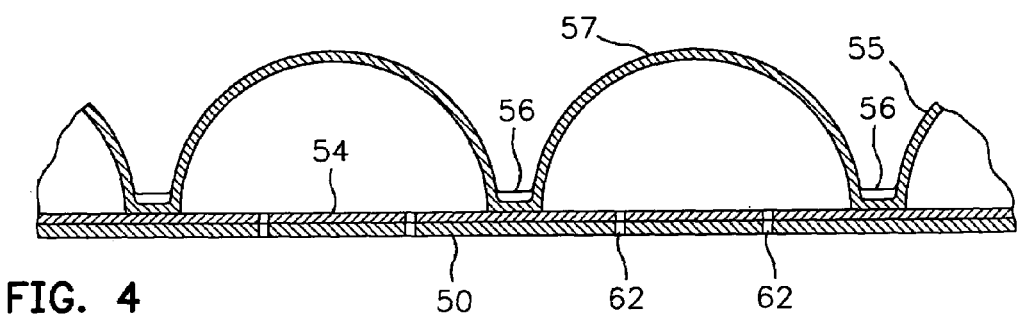
FIG. 4 is a further enlarged sectional view taken along line 4—4 of FIG. 3.

Construction details of the thermal blanket 10 are illustrated in FIGS. 3 and 4. The thermal blanket 10 is assembled from a base sheet consisting of an underside layer 50 formed from flexible material capable of bonding to a layer 52 of heat-sealable plastic. For the layers 50 and 52, we have used a stratum of absorbent tissue paper prelaminated with a layer of heat-sealable plastic. Material of such construction is commercially available in production rolls and is used to make painters' drop cloths. The upper side of the thermal blanket consists of a sheet of plastic bonded to the plastic layer 52 by an interruptible heat-sealing process to form the interrupted seams, one of which is indicated by 54, and the inflatable tubes, one indicated by 55. As can be seen in FIG. 3, the interruption of the seam 54 forms a passageway 56 between adjacent tubes 55 and 57.

The absorbent bib and tab are shown in FIG. 3 as a single material layer 60/58. Alternatively, they may be formed from separate material sheets cut to the outlines illustrated in FIG. 2. The absorbent material forming the bib and tab can be bonded to the upper plastic layer by heat process or by gluing.

The inventors also contemplate deletion of the bib and tab. In this instance, the thermal blanket would still have the viewing recess, which would be defined by the continuous seam at the head end, and which would be filled with the forward portion of the base sheet.

Circulation of heated air through the blanket is enhanced by the exhaust port openings 23, which open through the upper plastic sheet sheet, which is heat sealed to the base of the blanket. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket. We have measured the temperature distribution within the thermal blanket for inflating air which is heated to a medium temperature range and for inflating air which is heated to a high temperature range. The results are provided in Table I for a blanket consisting of 13 tubes. Measurements of the temperature of air exhausted through underside apertures were made on the underside of each tube on one side of the blanket. The tubes are numbered 1–6, with 1 being the tube adjacent to the center tube, and tube 6 being the outermost tube adjacent on lateral edge of the blanket. Test apertures were made in the bottom of tube 6 only for the purposes of this test. As is evident, the distribution of temperature within the erected thermal blanket is more uniform when the exhaust port openings are provided. Further, provision of the exhaust ports also increases the average temperature within the erected structure of the blanket. Clearly, the provision of exhaust port openings at the lateral edges of the blanket delivers results which one would not expect when considering the operation of our thermal blanket with no exhaust port openings.

In our first preferred embodiment, the exhaust port openings are slits in the edge seams of our blanket. These slits vary in length from 1¾ to 2 inches. Each edge seam is discontinuous approximately at each corner of the blanket so that inflating air is vented away form the underside of the erected blanket. This keeps the relatively "colder" air at the blanket edges form mixing with the relatively "hotter" air exhausted into the structure through the underside apertures. The result is a "flatter" temperature profile of air within the blanket than without the vents, which raises the average temperature within the erected structure and makes the temperature distribution in the structure more uniform. Resultantly, the clinical effect of the blanket is enhanced. Heating is better controlled, and more uniform, with greater comfort to the patient.

TABLE I

| TUBE NO. | MEDIUM TEMPERATURE RANGE | | HIGH TEMPERATURE RANGE | |
| --- | --- | --- | --- | --- |
| | WITHOUT EXHAUST PORTS | WITH 2" EXHAUST PORTS | WITHOUT EXHAUST PORTS | WITH 2" EXHAUST PORTS |
| center (inlet) tube | 113.3° F. | 114.1° F. | 121.3° F. | 121.3° F. |
| Tube #1 | 109.9° | 112.3° | 117.3° | 117.7° |
| Tube #2 | 105.3° | 109.8° | 113.4° | 115.0° |
| Tube #3 | 103.2° | 107.1° | 111.0° | 113.3° |
| Tube #4 | 99.9° | 104.3° | 101.4° | 108.6° |
| Tube #5 | 97.2° | 100.0° | 95.7° | 104.4° |
| Tube #6 (outermost) | 85.2° | 95.8° | 89.6° | 99.4° |
| Average temp. under cover | 103.8° | 106.7° | 108.4° | 112.5° |

Figure 5:
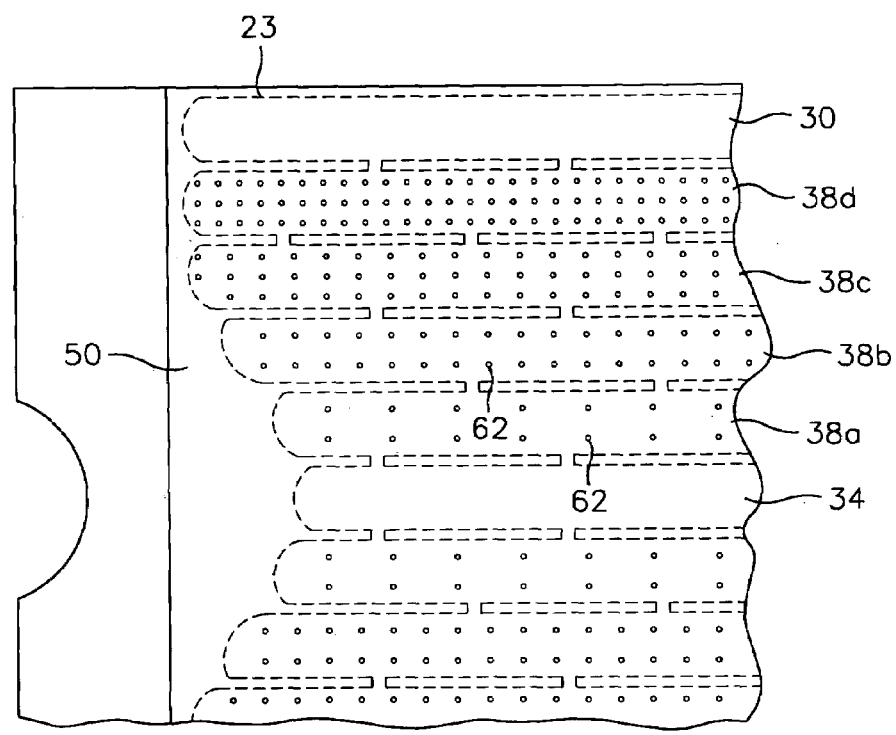
FIG. 5 is a partial underside view of the thermal blanket.

The thermal blanket of the invention is enabled to bathe a patient in the thermally-controlled inflating medium introduced into the upper side tubes by means of a plurality of apertures 62 shown in FIGS. 4 and 5. The apertures extend through the underside of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateral most tubes 30 and 32, or into the center tube 34. In addition, the apertures 62 are provided through the underside to the apertured tubes in a density which varies inversely with the proximity of the tube to the center tube 34. Thus, the hole density increases from the tube 38a through the tube 38d. Even with the exhaust port openings, the temperature of the inflating medium exhibits a drop from the center to the lateral most tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the thermal blanket. Therefore, fewer apertures are required for the tubes near the center tube 34 to deliver the same amount of air as the relatively greater number of apertures in the tubes at a greater distance from the center tube 34.

The apertures comprise openings which can be of any appropriate shape. For example, we have produced blankets with elongated apertures, approximately ¼ inch in length.

Figure 6:
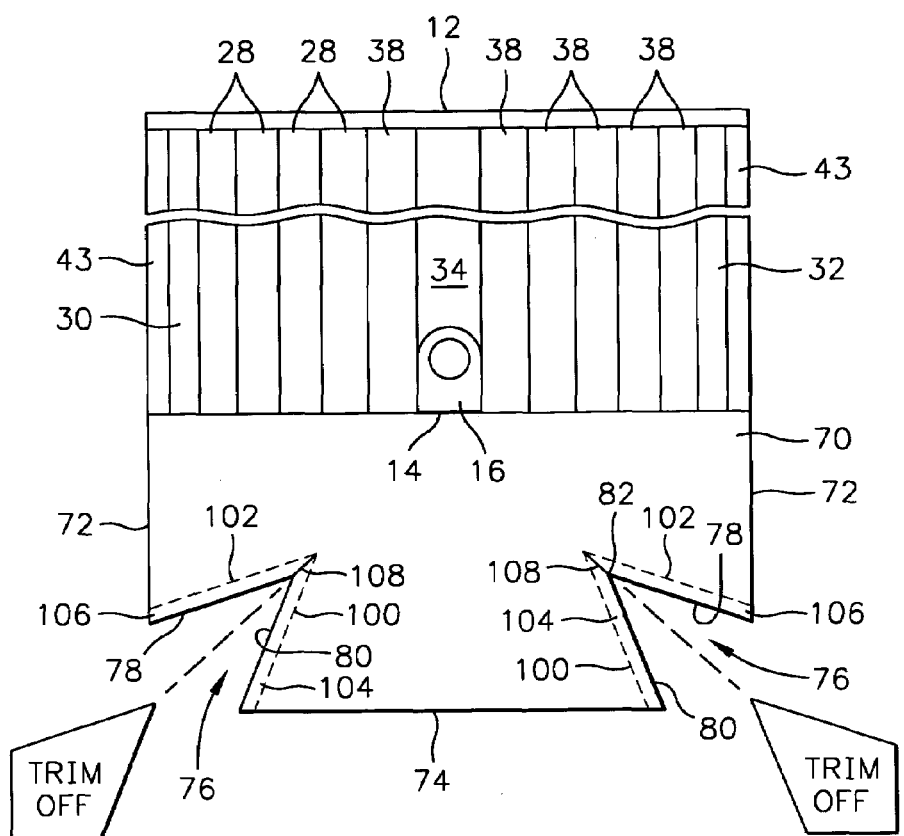
FIG. 6 is a partial diagrammatic top plan view of a thermal blanket constructed in accordance with a second aspect of the invention, with a partially constructed foot drape.
Figure 7:
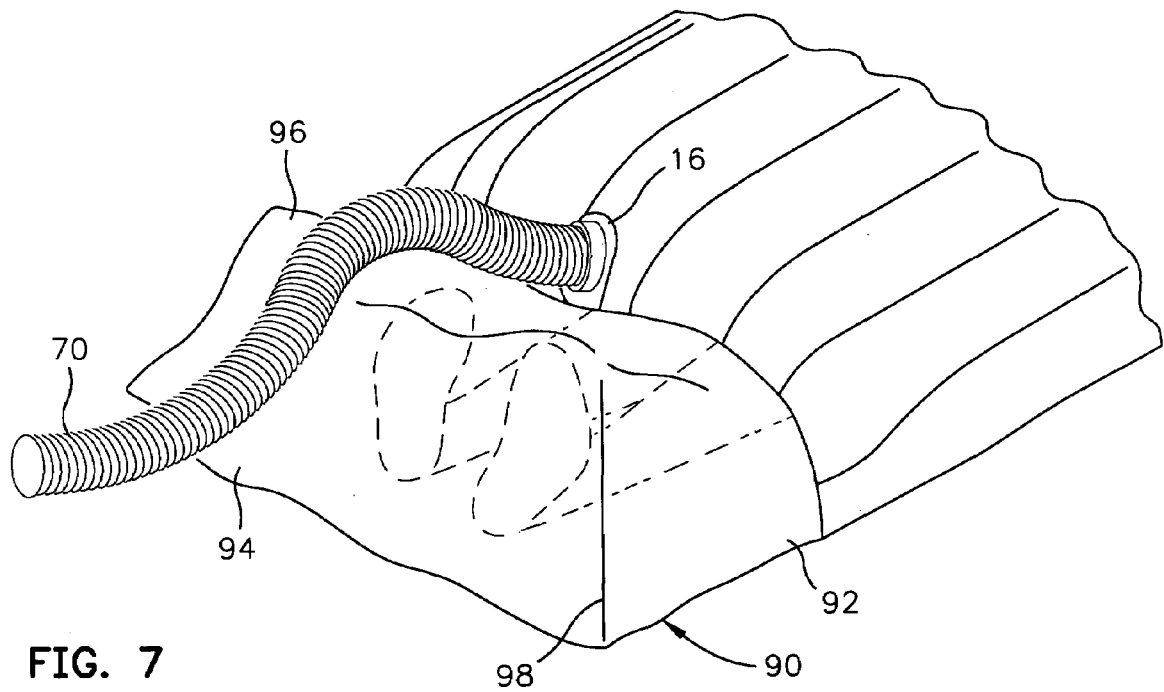
FIG. 7 is a partial projected view of a fully constructed thermal blanket of FIG. 6 in use, with the patient's feet illustrated by hidden lines underlying the foot drape.

Our invention is illustrated as we intend for it to be used in a second aspect including a foot drape in FIG. 7. The foot end 14 of the thermal blanket 10 is modified to provide an uninflated drape forming section 70 formed by a rearward extension of the base sheet 50/52 and a noninflatable portion of the heat-sealable plastic bonded to the base sheet. The drape forming sheet 70 has sides 72 extending parallel to and rearwardly from the outside edge of the edge seams 43, and a rear edge 74. Optionally, the drape-forming sheet 70 further includes a pair of V-shaped cuts 76 in the rear corners thereof. The V-shaped cuts 76 are formed by converging cuts 78 and 80, extending inwardly from one of the sides 72 and the rear edge 74, respectively, to a point of intersection 82. As shown in FIG. 7, the drape-forming section 70 may be formed into a foot drape 90 that includes a pair of side portions 92, a rear portion 94 and an upper portion 96. The drape 90 is so formed by joining the edges 78 and 80 of the V-shaped cuts 76 to form a pair of seams 98. To form the seams 98, the V-shaped cut edges 78 and 80 may be folded about respective lines 100 and 102 that parallel the edges 78 and 80, as shown in FIG. 6. The resulting respective folded surfaces 104 and 106 may then be fastened together by appropriate means such as heat sealing. Joining the surfaces 104 and 106 forms a crease 108 and transforms the two dimensional drape forming section 70 into the three dimensional drape 90.

The resultant drape 90 is non-inflatable but erectable under the force of the heated medium circulating around the patient. The drape 90 thus traps and retains heat around the patient's feet to warm the feet. As shown in FIG. 7, the drape 90 also insulates the bare skin of the feet from excessive conductive heat from the inflating hose 70 in the event the hose is oriented in a position wherein it might otherwise come in contact with the feet. Patient warming and comfort is thus further enhanced.

Figure 8:
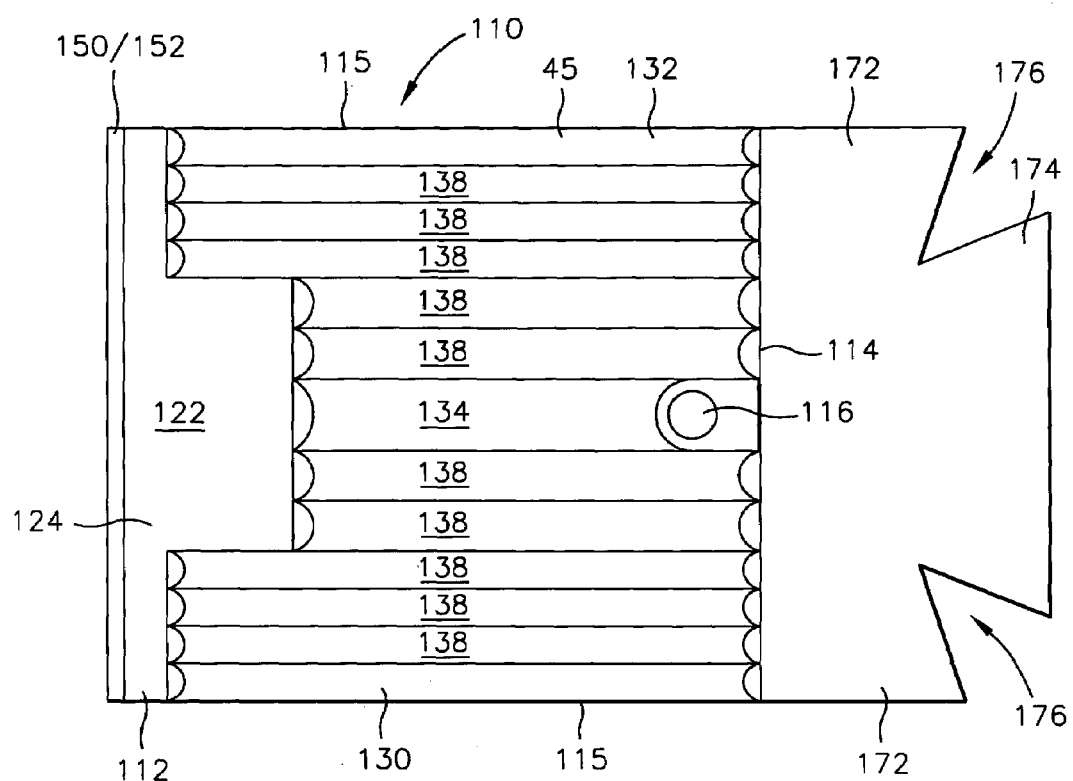
FIG. 8 is a top plan view of a partially constructed thermal blanket in accordance with a third aspect of the invention, for thermally covering the pelvic area and lower extremities of a patient.
Figure 9:
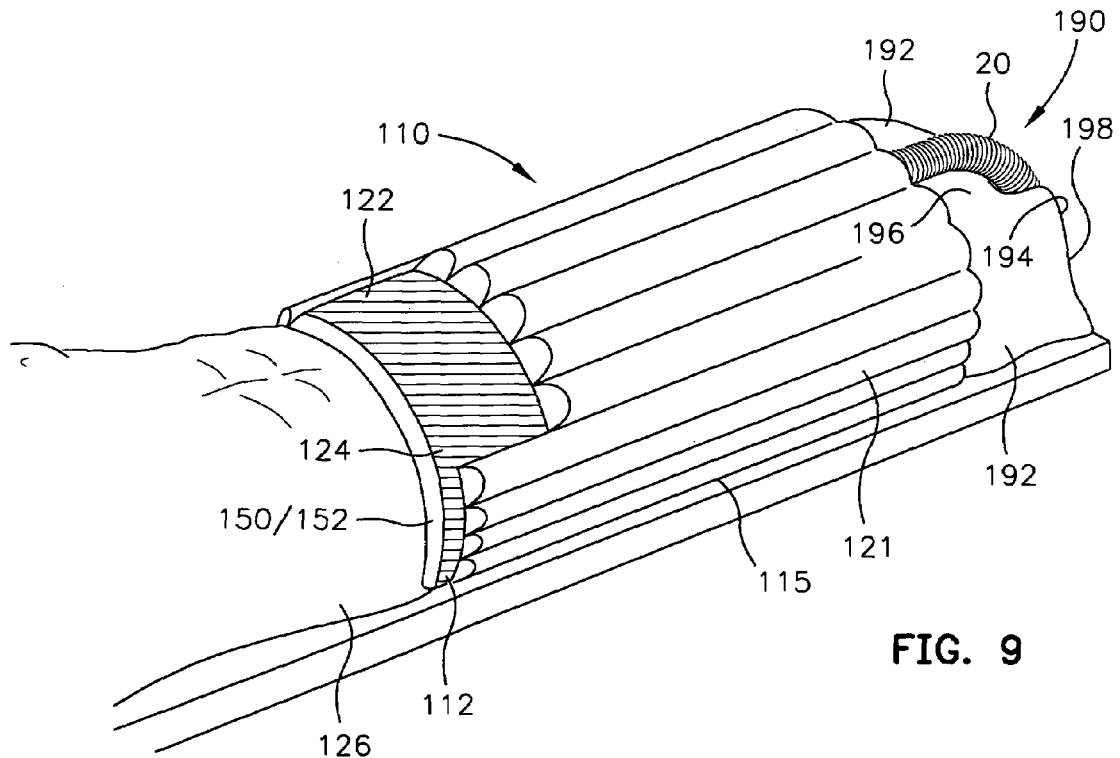
FIG. 9 is a partial projected view of a fully constructed thermal blanket of FIG. 8 in use.

Our invention is illustrated as we intend for it to be used in a third aspect as an inflatable lower body covering in FIGS. 8 and 9. This covering warms convectively by exhausting warm air onto a patient. The thermal covering in this case is similar in all respects to the covering shown in FIGS. 6 and 7, except that the covering may be shortened to cover only the pelvic area and lower extremities of the patient. Moreover, the head end of the covering may be modified to provide an open flat working area for the placement of instrumentation and to improve visualization of the care site, as shown in FIG. 9. As in the case of the thermal coverings discussed above, the covering 110 of FIGS. 8 and 9 includes a head end 112, a foot end 114, a pair of lateral edges 115, and an inflation inlet cuff 116 to which may be connected through a heater tube 20 to a heater/blower assembly such as the assembly 18 shown in FIG. 1. As shown in FIG. 9, the covering 110 may be inflated to form a Quonset hut-like structure with a quilted upper surface 121. Like the thermal covering 10, a pattern of apertures on the undersurface of the blanket 110 convectively delivers the inflating heated air into the interior space enclosed by the erected thermal blanket.

Alternatively, the head end of the quilted upper surface 121 could extend directly from one edge 115 to the other edge 115 without the provision of a non-inflated blanket recess 122, as shown in FIG. 8. Further, an adhesive strip 124 made of an adhesive material may be attached to the head end 112 of the covering 110 and extend between the edges 110. As shown in FIG. 8a, the adhesive strip 124 is mounted with its adhesive side oriented toward the base sheet, which includes an underside layer 150 formed from a flexible material capable of bonding to a layer 152 of heat sealable plastic. The layers 150/152 are formed in the same manner as the layers 50/52 shown in FIG. 3 and described above. Mounted to the underside of the adhesive strip 124 is a backing strip 125, which may be positioned partially between the adhesive strip 124 and the layer 152 to prevent inadvertent peel-off.

As shown in FIG. 9, the adhesive strip 124 may be adhered above the patient's pelvic and groin area to prevent the migration of air from inside the covering 110 to the care site. Moreover, the optional non-inflated recess 122 may be large and well-defined in order to improve visualization of the operating field and provide sufficient working area for resting instruments or other items during the rendering of care to a patient 126.

Like its counterpart covering 10, the covering 110 includes a parallel array of elongated tubes of which 130 and 132 are the lateralmost tubes, 134 is the center tube, and the tubes 138 are arrayed between one of the lateralmost tubes and the center tube. The thermal covering 110 further includes a non-inflated yet erectable foot drape for retaining a thermal medium around a patient's feet. As in the covering shown in FIG. 6, the covering 110 is provided with a non-inflated drape forming section 170 extending rearwardly from the foot end 114. The covering 170 includes a pair of sides 172 and a rear edge 174. Moreover, the drape forming sheet 170 includes a pair of V-shaped cuts 176 in the rear corner thereof. As shown in FIG. 9, the drape forming section 170 may be formed into an erectable foot drape 190 that includes a pair of side portions 192, a rear portion 194, and an upper portion 196. As in the covering 10, the drape 190 of the covering 110 is formed by joining the edges of the V-shaped cuts 176 to form a pair of seams 198.

As with the longer full-body thermal blanket of FIGS. 1 and 2, the covering 110 may be provided without a foot drape as appropriate. In that case, it may be desirable to slideably mount a protective sleeve 200 over the connecting hose 20 to prevent the tube from contacting the patient.

Advantageously, it will be observed that the lower body warming cover 110 maintains a thermal medium around the pelvic and groin area and lower extremities of the patient, while at the same time exposing the patient's torso and head as may be necessary for the provision of medical care and treatment to those areas.

Figure 10:
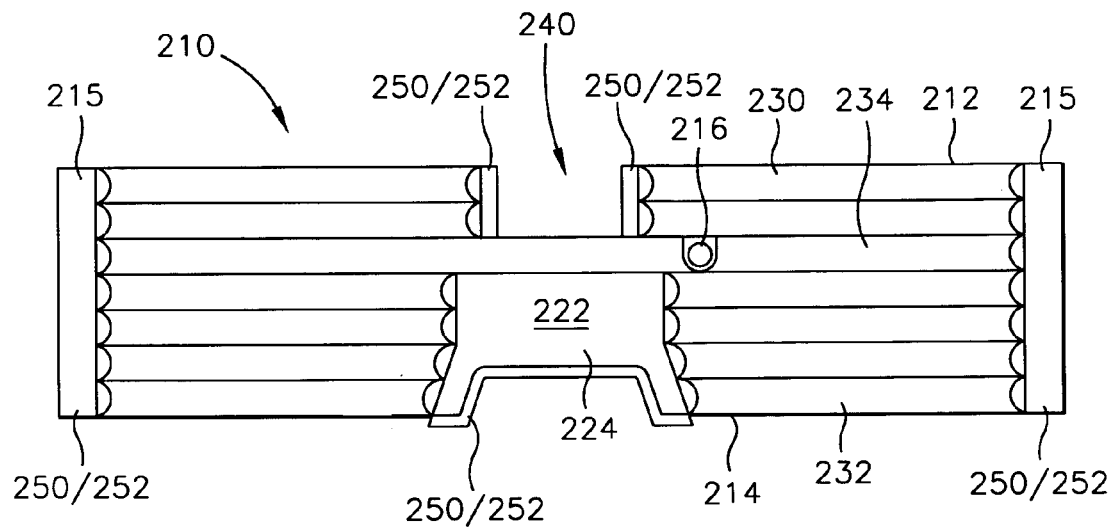
FIG. 10 is a top plan view of a thermal blanket constructed in accordance with a fourth aspect of the present invention, for thermally covering the chest and upper extremities of a patient.
Figure 11:
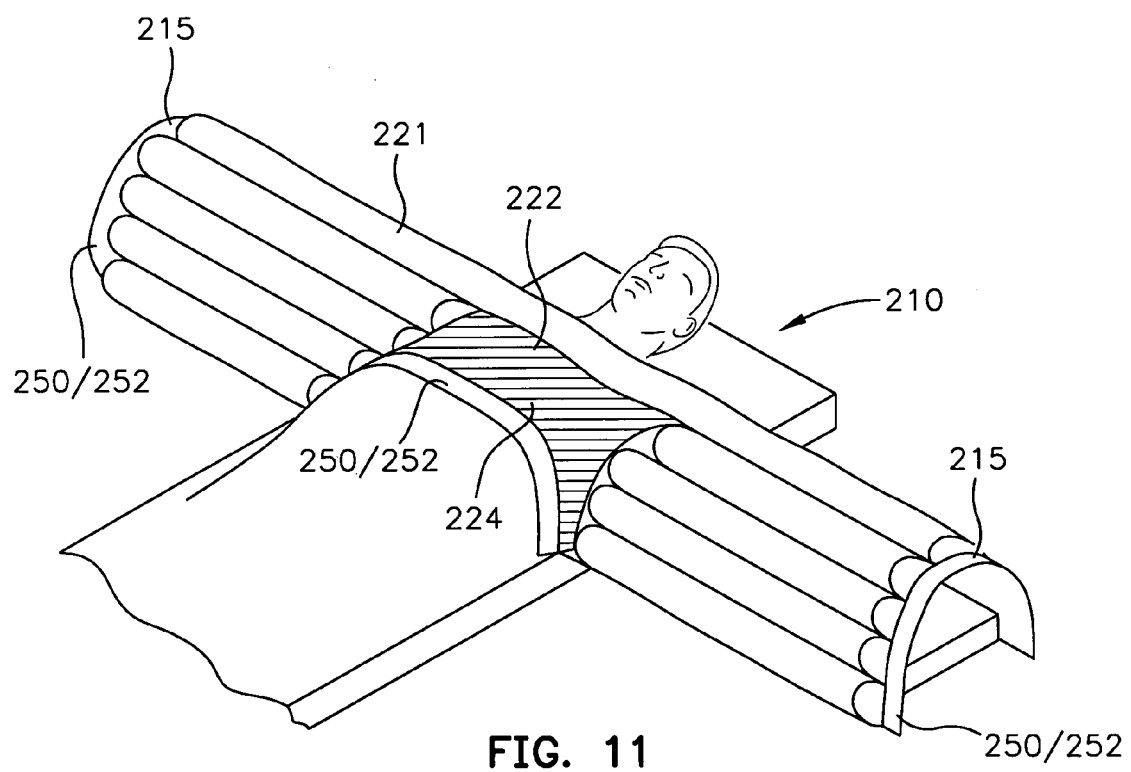
FIG. 11 is a partial projected view of a fully constructed thermal blanket of FIG. 10 in use.

Alternatively, or in combination with the lower body thermal covering 110, an upper body thermal covering 210 could be provided as shown in FIGS. 10 and 11. The upper body thermal covering 210 is structurally and functionally similar in most respects to the thermal coverings 10 and 110 discussed above. Thus, the thermal covering 210 includes a head end 212, a foot end 214, a pair of lateral edges 215, and an inflation inlet cuff 216 which may be connected through a connecting hose 20 to an external heater/blower assembly such as the assembly 18 shown in FIG. 1. The thermal covering 210 further includes a quilted upper surface 22, which may have non-inflated recess 222 located at the foot end of the covering, as shown in FIG. 11. Thus, with the upper torso and arms of the patient being thermally bathed, the uninflated recess 222 permits observation of the patient's middle torso from almost any location with respect to the thermal covering 210.

Alternatively, as shown in FIG. 10, the quilted upper surface 221 could extend across the entire expanse of the covering between the edges 215 such that no uninflated recess 222 is formed. It is preferable in most cases, however, to provide a recess 223 in the quilted upper surface 221 and the foot end 214 of the covering 210 to accommodate the curvature of the patient's torso, as shown in FIG. 11.

There may be additionally provided an adhesive strip 224 mounted to the foot end 214 of the covering 210. As shown in FIG. 10a, the adhesive strip 224 is mounted with the adhesive side facing the base sheet, which includes an underside layer 250 formed from a flexible material capable of bonding to a layer 252 of heat sealable plastic. The layers 250/252 are formed in the same manner as the layers 50/52 shown in FIG. 3 and described above. Mounted to the underside of the adhesive strip 224 is a backing strip 225, which may be positioned partially between the adhesive strip 224 and the layer 252 to prevent inadvertent peel-off. As shown in FIG. 11, the adhesive strip 224 may be adhered to the patient's torso to prevent the migration of air toward the care site.

The covering 210 further includes an array of elongated tubes of which 230 and 232 are the lateral most tubes, 234 is the center tube and the tubes 238 are arrayed between one of the lateral most tubes and center tube. In addition, the thermal covering 210 includes a cutout area 240 centrally positioned at the head end 212 of the covering. The cutout 240 is formed by truncating the lateralmost tube 230 and an adjacent tube 238. The recess 240 permits observation of the patient's head and neck from almost any location with respect to the thermal blanket 210. It also assists in thermally covering the patient's shoulders and arms without covering the patient's face. As shown in FIGS. 10 and 11, the bottom layer 250/252 of the covering 210 may extend slightly beyond lateral edges 215 or the head end 212, or it may be coextensive therewith.

As shown in FIG. 11, the thermal covering 210 is positioned over the patient's upper torso and arms so as to thermally control those areas while leaving the patient's lower torso exposed for the provision of care. As indicated, the thermal covering 210 may be used alone or in combination with the thermal covering 110 depending on the location of the care site. Thus, various selected portions of the patient may be selectively warmed with the illustrated thermal coverings while care and treatment may be rendered to other areas. In addition, a plastic head drape 260 may be adhesively mounted to the covering 210 over the patient's chest, and adjacent the head end 230. The plastic head drape 260 is placed over the patient's head and one or more vents 270 may be provided to direct warmed air to the head area.

In a preferred method of operation, one or both of the coverings 110 and 210 may be selectively employed on a patient to warm selected portions of the patient while permitting other portions to remain exposed for treatment. In utilizing the coverings 110 and 210, either alone or in combination, the covering 110 or 210 is first placed over the patient. The adhesive backing 125 or 225 is removed from the adhesive strip 124 or 224 and the adhesive strip is adhered to the patient to prevent the migration of air toward the care site. The hose 20 is then attached to the covering, an appropriate temperature is selected on the heater unit 18 and the unit 18 is activated. For the covering 110, the protective heater tube 200 cover may also be used when the cover does not include a foot drape. For the covering 210, the head drape 260 may be adhered to the quilted portion 221 over the patient's chest and draped over the patient's head. As a final measure, a conventional blanket may be placed over the covering 110 or 210. During operation, the patient's temperature should be monitored regularly and the air temperature setting of the heater unit 18 adjusted accordingly.

Many modifications and variations of our invention will be evident to those skilled in the art. For example, thermal coverings for additional selected patient areas could be implemented depending on the location of the care site and the need for thermally maintaining other areas. It is understood that such variations may deviate from specific teachings of this description without departing from the essence of the invention, which is expressed in the following claims.

We claim:

1. An inflatable thermal blanket for covering and bathing a portion of a patient's body with thermally-controlled air, comprising:
   a flexible base sheet having a first end forming a first end of the thermal blanket, a second end forming a second end of the thermal blanket, two edges forming respective edges of the thermal blanket, and an undersurface forming an undersurface of the thermal blanket;
   the first end, the second end, and respective edges of the base sheet forming a periphery of the thermal blanket;
   the base sheet including a first layer of flexible material and a second layer of plastic material co-extensive with, and laminated to, the first layer of flexible material;
   an overlying flexible material sheet attached to the layer of plastic material by a plurality of seals to form the base sheet and the overlaying sheet into an inflatable covering;
   a seal between the overlaying material sheet and the base sheet around the periphery;
   said inflatable covering for substantially longitudinal disposition over a portion of said patient's body extending substantially from the pelvic area of said patient's body to the feet of said patient's body;
   an inflating inlet for admitting thermally controlled air into the inflatable covering;
   a plurality of apertures opening through the base sheet into the inflatable covering for exhausting thermally controlled air from the inflatable covering; and
   a non-inflatable foot extension formed in the inflatable covering at the second end for covering and warming said patient's feet.

2. The inflatable thermal blanket of claim 1, wherein said thermal blanket is self-erecting.

3. The inflatable thermal blanket of claim 1, wherein the non-inflatable foot extension comprises a non-inflatable extension of the inflatable covering beyond the second end.

4. The inflatable thermal blanket of claim 1, wherein the non-inflatable foot extension includes an extension of the base sheet beyond the second end.

5. The inflatable thermal blanket of claim 1, wherein the plurality of seals are discontinuous elongate seams formed between the overlaying material sheet and the sheet of plastic material.

6. The inflatable thermal blanket of claim 5, wherein the discontinuous elongate seams form the overlaying material sheet into a plurality of inflatable chambers, the plurality of inflatable chambers including parallel, communicating tubular chambers.

7. The thermal blanket of claim 5, wherein the non-inflatable foot extension includes an extension of the base sheet beyond the second end.

8. A thermal care system including the inflatable thermal blanket of claim 1, and further including:
 a heater/blower assembly for providing a source of heated air; and
 a connecting hose coupled to the heater/blower assembly and to the inflating inlet for conducting heated air from the heated/blower assembly into the inflatable covering.

9. A method of warming a patient using a thermal blanket including an inflatable space formed between a flexible base sheet and an overlaying material sheet attached to the base sheet by a peripheral seal around the periphery of the thermal blanket and a plurality of seals inside the periphery of the thermal blanket, a non-inflatable section formed in a portion of the inflatable thermal blanket, and apertures that open into the inflatable space through the flexible base sheet for exhausting air from the inflatable space, the method comprising the steps of:
 disposing the thermal blanket to substantially longitudinally dispose the inflatable space over a portion of a patient's body extending substantially from the pelvic area of said patient's body to the feet of said patient's body, with the non-inflatable section disposed over the patient's feet;
 inflating the thermal blanket with warmed air;
 exhausting warmed air through the apertures in the flexible sheet; and
 using the non-inflatable section, retaining heat under the thermal blanket near the patient's feet.

10. The method of claim 9, wherein the thermal blanket is a self-erecting thermal blanket, the method further comprising the step of:
 the inflatable thermal blanket self-erecting in the step of inflating.

* * * * *

UNITED STATES PATENT AND TRADEMARK OFFICE
CERTIFICATE OF CORRECTION

PATENT NO. : 7,101,389 B1
APPLICATION NO. : 08/419719
DATED : September 5, 2006
INVENTOR(S) : Augustine et al.

It is certified that error appears in the above-identified patent and that said Letters Patent is hereby corrected as shown below:

Title Page
Under the heading RELATED U.S. APPLICATION DATA, column 1, line 64, delete "now Pat. No. 5,405,371" and replace it with --Pat. No. 5,405,371, which was reissued as RE38,462--.

Column 1, line 7
After "5,405,371" add --which was reissued as RE38,462, which--.

Column 1, line 14
After "08/386,324" add --, abandoned--.
After "08/388,730" add --, U.S. Pat. No. 5,620,482--.
After "08/419,718" add --, abandoned--.

Column 5, line 59
Delete the duplicate recital of the word "sheet".

Column 6, line 23
Delete the word "form" and replace it with --from--.

Column 6, line 25
Delete the word "form" and replace it with --from--.

Column 8, line 54
Delete the word "tube" and replace it with --hose--.

Signed and Sealed this

Eighth Day of July, 2008

JON W. DUDAS
*Director of the United States Patent and Trademark Office*